United States Patent [19]

Haynes

[11] 4,129,501

[45] Dec. 12, 1978

[54] METHOD AND APPARATUS FOR DETECTING WATER IN OIL

[76] Inventor: Edward M. Haynes, Box 197, Clifton Forge, Va. 24422

[21] Appl. No.: 831,164

[22] Filed: Sep. 7, 1977

[51] Int. Cl.² .............................................. B01D 13/00
[52] U.S. Cl. ................ 210/23 R; 210/96 R; 210/100; 210/258; 210/497 R; 324/65 R; 200/61.05
[58] Field of Search .............. 324/65 R, 65 P; 338/34, 338/35; 73/73, 61.1 R; 210/100, 23 R, 96 R, 258, 497 R; 137/2, 5; 200/61.05, DIG. 40, DIG. 41

[56] References Cited

U.S. PATENT DOCUMENTS

| | | | |
|---|---|---|---|
| 2,583,930 | 1/1952 | Cotton | 324/65 R X |
| 2,636,962 | 4/1953 | Bouyoucos | 324/65 R X |
| 2,681,571 | 6/1954 | Becher | 324/65 R X |
| 2,976,728 | 3/1961 | Brogan et al. | 324/65 R X |
| 3,295,088 | 12/1966 | Smith | 338/35 |
| 3,376,501 | 4/1968 | Peranio | 324/65 R X |
| 3,458,845 | 7/1969 | Thoma | 338/35 |
| 3,493,484 | 2/1970 | Berg et al. | 324/65 R |
| 3,522,530 | 8/1970 | Muller | 324/65 R |
| 3,800,219 | 3/1974 | Fosberg | 324/65 R |
| 3,916,674 | 11/1975 | Miller et al. | 324/65 R X |

FOREIGN PATENT DOCUMENTS 1399477  4/1965  France ................................. 324/65 R

*Primary Examiner*—Stanley T. Krawczewicz
*Attorney, Agent, or Firm*—W. Allen Marcontell

[57] ABSTRACT

A sheet of hydrophilic paper is laminated between two plate electrodes and immersed as a water sensor assembly in an electric power transformer oil charging flow stream. A low power and voltage d.c. potential is impressed across the plates as the oil flows through or around the sensor. Any water in the flow stream coming into contact with the paper is absorbed and retained thereby. Such water reduces the electrical resistance of the paper thereby causing current flow. The consequent current flow is used as a signal to initiate the operation of a series of relays which interrupt the power supply of a prior art filtration drive motor.

7 Claims, 7 Drawing Figures

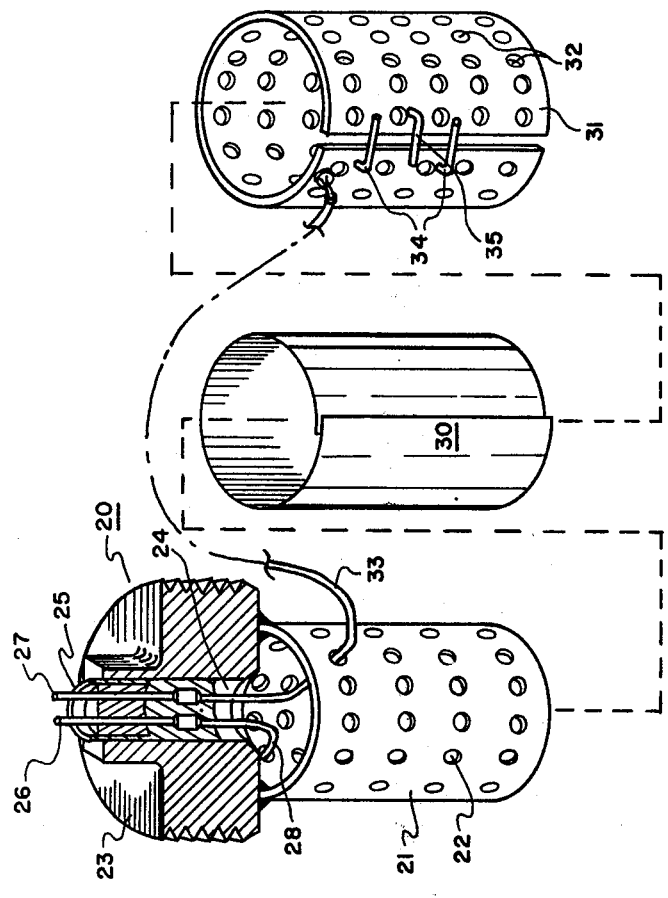
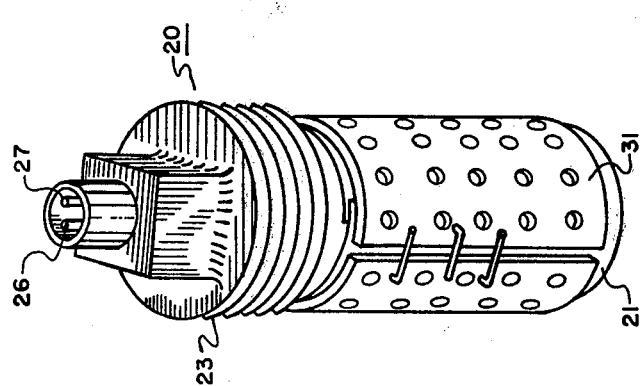
FIG. 4
FIG. 3

METHOD AND APPARATUS FOR DETECTING WATER IN OIL

BACKGROUND OF THE INVENTION

1. Field of the Invention

The present invention relates to apparatus and methods for detecting the presence of water in a petroleum fluid.

2. Description of the Prior Art

Electrical power transformers of the size and capacity used by commercial power utilities to maintain primary transmission line voltage are normally charged with a petroleum fluid called insulating or dielectric oil for the dual purpose of insulating the primary and secondary transformer windings, each from the other, and also as a cooling medium to remove inductance heat from the proximity of the transformer core and windings.

Such dielectric oil is also used in relays, switches, oil circuit breakers, and other large capacity power transmission equipment. For brevity, the following description will hereafter be related to transformers, but it will be understood that all such oil insulated transmission devices are included.

In operation, the oil reservoir of such transformers is sealed from the atmosphere. However, if the unit is to be moved from one operating location to another, it is often necessary to remove the oil for weight reduction.

Oil is also removed from a transformer periodically to filter an accumulation of colloidally dispersed carbon particles from the fluid which develop due to localized overheating of the hydrocarbon substance in the course of operation.

It is during these occasions of field removal and recharging that opportunity is given for moisture infusion into the system.

The primary objection to moisture in the oil charge is that water concentrations above a very low threshold percentage reduce the dielectric characteristic of the oil (increase the conductance) sufficiently to permit arcing across the windings. Since the e.m.f. between the windings may be in the order of 1000 v or more, once the arc begins, it is sustained and intense. Consequently, rapid thermal dissociation of the hydrocarbon compounds occurs to generate catastrophic pressure increases within the sealed transformer housing. Transformer explosion is the terminal result.

Although great care is normally taken during the oil charging and cleaning process, precautionary procedures are, nevertheless, subject to occasional human failure. As a result of such occasional failures and the enormous expense for repair or replacement of the damaged equipment, the consequent economic burden is a significant factor in the operating overhead of utility companies.

One of such precautionary procedures practiced universally is a final, full-flow filtering of the oil as it is returned to the transmission equipment reservoir. Presently, two types of such filters are predominately used.

One type of such filters is a laminated plate assembly wherein a series of perforated steel plates are separated by sheets of "blotter paper." A specification of such paper may be 25 mil thickness and approximately 26 pounds per cubic foot density. As specified by one manufacturer of such paper, the Eaton, Dikeman Co. of Mt. Holly Springs, Pa. 17065, the paper is 25 caliper, 75 pounds per 500, 20 in. × 20 in. sheets. This paper is believed to be substantially pure, bleached cellulose except for the inclusion of less than 0.1% melamine formaldehyde. The controlling characteristics of this blotter paper for the present purposes is the high permeability and affinity for water thereof. The fact that the fiber surfaces may be completely surrounded by oil as in the case of complete immersion, does not diminish the capacity of the fiber to absorb water coming into contact therewith.

The foregoing description of such blotter paper will hereafter serve as a definition of the term "hydrophilic material" and permeations thereof. There are other manufacturers of suitable blotter paper and the thickness and density may vary over a wide range. However, the characteristic capacity to absorb water in the immersed presence of oil is critical. An electrical characteristic of this hydrophilic material critical to the present invention will subsequently be described.

Another filter type widely used by the utility industry for charging transformers and relays is a cartridge type. The basic construction of such cartridge filters comprises inner and outer perforated cylindrical sleeves separated by a packed annulus of hydrophilic filter material. In this case the filter material is substantially less compacted than that of the machine laid sheet described above but the flow passage (radial) thickness is substantially greater. Consequently, the absolute fiber quantity contacted by the oil as it flows radially outward from the inside bore of the interior sleeve and across the filter annulus to the exterior sleeve may be at least as great or greater.

Although there are many devices and techniques for separating water from oil, the aforedescribed filters are distinct in their capacity to absorb and retain small quantities of water that is distributed about the oil mass in isolated pockets or discrete droplets. However, such filters are also subject to saturation of this capacity. Such a water saturated filter is useless. Unfortunately, operator knowledge of such saturation is quite another matter. Consequently, filter elements are replaced on a routine schedule based on volumetric throughput of oil. The cost of maintenance labor and filter element replacement contribute to balance a probability equation which dictates maintenance frequency. In operation, however, such filters are usually replaced when only 30% or less saturated. Nevertheless, occasionally a fresh filter becomes saturated in the process of a single charge thereby permitting sufficient water to pass into the equipment to cause damage. Prior to the present invention, no device or procedure was available to positively prevent such occurrences.

PRIOR ART STATEMENT

The presence of water dispersed in petroleum fluid is a problem in the operation of equipment other than that for electrical power transmission. The operation of jet aviation engines is also adversely affected by such contamination. Consequently, numerous prior art methods and apparatus have been devised to detect and signal the presence of water in petroleum.

Judging from numerical preponderance in the patent literature, it would seem that the prior art has predominately sought solution for the stated problem by means of a capacitative sensor. The following U.S. Pat. Nos. are representative: 3,961,246; 3,878,461; 3,876,916; 3,793,585; 3,622,875; 3,596,176; 3,508,435; 3,481,182; 3,263,492; 3,238,452; 3,155,900; and 3,155,899. In all of the foregoing disclosures, operative reliance is predicated on the dielectric property of the petroleum and the change therein when contaminated with water. However, when the water is present in relatively minute quantities dispersed throughout the fluid mass, no change in the oil dielectric strength is detected except at the moment a water pocket passes the sensor. If the flow rate is great and the pockets few and far between, only a momentary variation in the oil dielectric strength will be indicated. Other innocent anolomies in the flow mass may also cause the same indicator response. If such water remained dispersed throughout the fluid mass, it might be possible to utilize such serveillance devices with modification for the present purposes. However, it is suggested that under the operating conditions of electric power transmission, the originally dispersed water conglomerates to form a single, damaging mass. Moreover, due to the fact that capacitance is the measured electrical characteristic, most of the above patent disclosures also include complex oscillator circuits subject to thermal and atmospheric humidity drift to energize the capacitative sensor.

U.S. Pat. No. 2,682,168 is an exceptional prior art disclosure in that a "moisture-sensitive solid insulation" member is described as immersed in the oil of a transformer tank. Separate electrodes are secured to this solid insulation member and project through the tank walls. The inventor states that the power factor of the transformer is a function of the insulation dryness and may be determined by impressing a known potential e.g. 3000 volts across the electrode terminals and measuring the ohmic losses across the insulation. A careful examination of this vague disclosure will disclose that the "moisture-sensitive solid insulation" is not described in direct terms but rather, implied to be a respresentative sample of the winding insulation. Such insulation is normally heavily impregnated with phenolic resins and would not be characterized by the normal lexicon as "moisture-sensitive." In fact, much effort is devoted to render such insulating material moisture resistant or at least moisture stable. By no stretch of the language could such insulating material be characterized as hydrophilic.

In contrast with the prior art, an object of the present invention is to teach a method and apparatus for monitoring a very small total quantity of water dispersed within a large quantity oil.

Another object of the present invention is to stop the transfer of water contaminated oil into a protected transformer unit by automatically stopping the transfer pumps.

Another object of the present invention is to permit maximum utilization and saturation of full-flow line filters having the purpose of removing water from a transfer flow stream.

Another object of the invention is to reduce the cost of oil charging equipment maintenance by providing a device which informs the equipment operator with a positive signal indication that the water filter capacity of such charging equipment is saturated notwithstanding length of service time or volumetric throughput.

Another object of the invention is to provide, within an oil flow stream, a moisture responsive sensor having the safety feature of a standing, low voltage, d.c. energy charge.

Other objects of the invention will become apparent from the following description.

SUMMARY OF THE INVENTION

These and other objects of the invention are accomplished by means of a hydrophilic insulator separating two electrodes in a flow-stream immersed assembly. A hydrophilic insulator is a fluid permeable material which, like the hydrophilic blotter paper described above, also demonstrates the property of high dielectric capacity when dry (free of water albeit wet with oil) and low dielectric capacity when wet with water. The 0.025 in. thick, 26 lb/ft.$^3$ bleached cellulose sheet treated with less than 0.1% melamine formaldehyde as manufactured by Eaton, Dikeman Co. supra, is such a material. There are others of differing caliper and density.

The assembly electrodes are charged with a low standing potential, in the order of 12 volts. One electrode is in bridge circuit with the base terminal of a semiconducting device. When the hydrophilic insulating material is permeated by water, the resistance thereof to the standing potential across the electrodes in contact therewith falls with the consequence of initiating a current flow through one leg of the bridge circuit thereby raising the bias voltage on the semiconductor base terminal. This circumstance initiates an actuating current which is amplified and used to open relay contacts in the power supply circuit of the oil pump motor, thereby stopping the pump.

BRIEF DESCRIPTION OF THE DRAWING

Relative to the drawing wherein an identity of reference characters is used throughout the several figures to designate the same or similar elements:

FIG. 3 is an assembly detail of one form of the present sensor element.

FIG. 4 is an exploded detail of the sensor illustrated in assembly by FIG. 3.

DESCRIPTION OF THE PREFERRED EMBODIMENTS

Figure 1:
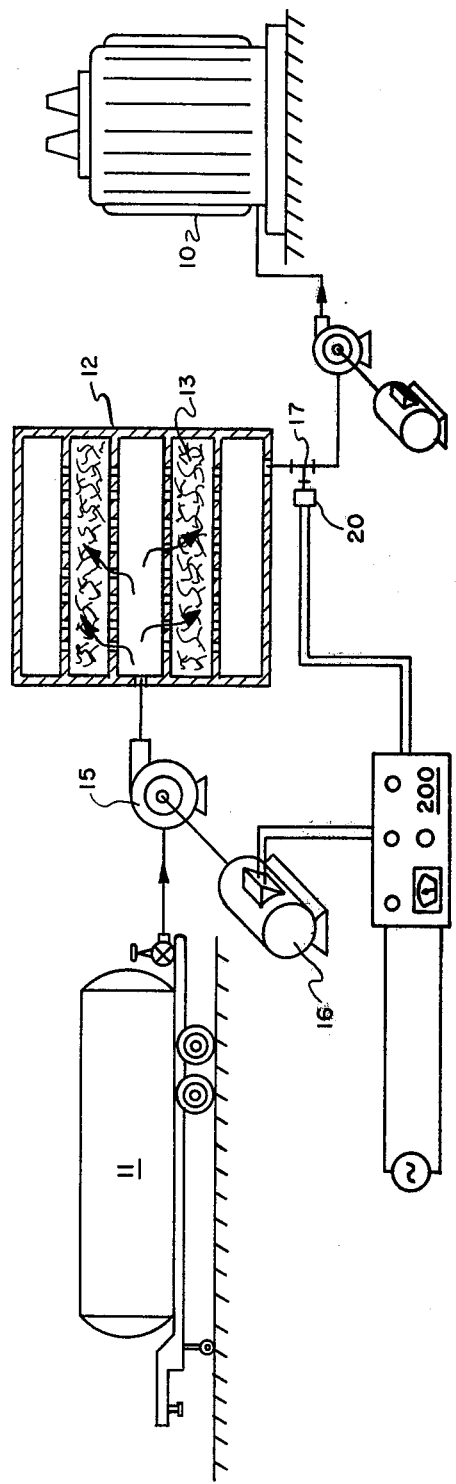
FIG. 1 is a schematic illustrating the use environment of one embodiment of the invention.

Relating the schematic of FIG. 1 to the preferred application of the invention, there is shown a unit of power transmission equipment such as transformer 10 connected to receive dielectric oil from a tank carrier 11. Interposed within the transfer conduit is a full flow cartridge filter 12 packed with hydrophilic filtration material 13. Filter pump 15 driven by motor 16 forces the oil past the high pressure losses presented by the filtration material 13 and into the inlet of a secondary transfer pump which discharges into the oil reservoir of transformer 10.

Within this prior art filtration system, one embodiment of the present invention sensor is connected as a cartridge insert 20 to a pipe T-fitting 17 within the flow conduit downstream of the filter unit 12.

Primary power to the filter pump motor 16 is controlled by console circuitry 200 which responds to signals or electrical characteristics received from sensor 20 to interrupt power to the motor 16 when sufficient quantity of water permeates the sensor.

Figure 2:
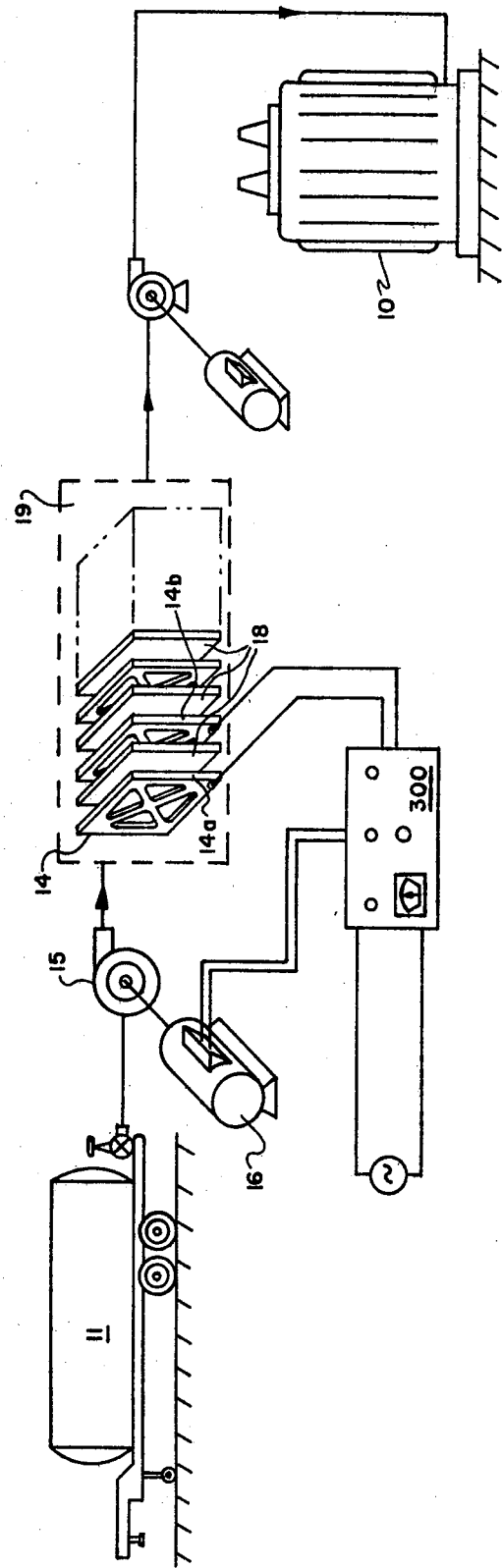
FIG. 2 is a schematic illustrating the use environment of another embodiment of the invention.

The filter system of FIG. 2 represents the other of two presently predominating filter systems used for transformer charging and primarily differs from the FIG. 1 system by the filter unit 19. The unit 19 comprises a case or housing represented by the dashed line boundary which encloses a multiplicity of perforated plates 14 separated by sheets 18 of hydrophilic filter material. Like the cartridge 12 of FIG. 1, the filter unit 19 also is a full flow device wherein all the incoming dielectric oil must pass through the filter sheet elements 18. A protective circuit responsive to electrical characteristics unique to the filter sheet 18 material is housed by console 300. Sensor controlled relays within the console 300 circuitry serve to interrupt the power flow to filter motor 16 when water permeates the sheets 18.

Referring now to the cartridge sensor element 20, per se, as used in combination with the cartridge filter system of FIG. 1, there is shown by FIG. 3 a pictorial of the assembly. FIG. 4 is a partially sectioned disassembly of the cartridge 20 components. Further regarding FIG. 4, there is shown a cylindrical ground plate 21 thoroughly perforated with apertures 22. Preferably, the unground plate 21 is fabricated from stainless steel and is welded at one axial end thereof to a stainless steel pipe plug 23. Through the center of plug 23 is drilled a bore hole 24 to receive a moisture-proof connector base 25 having at least two connecting pins 26 and 27 bedded in an insulating potting compound. Ground wire 28 electrically connects pin 26 to the ground plate 21.

Around the ground plate 22 is wrapped a small sheet or strip of the aforedescribed hydrophilic filter material 30 resembling conventional desk blotter paper. Concentrically surrounding the blotter paper 30 is a split, cylindrical sleeve 31, also fabricated from stainless steel. Apertures 32 thoroughly perforate the surface of sleeve 31 to permit intimate contact of the blotter 30 with the oil flow stream. Insulated conductor 33 electrically connects the sleeve 31 with connector pin 27. Lugs 34 and 35 facilitate manual spreading of the split sleeve for removal and assembly when the blotter 30 is changed.

By comparing the plate assembly 19 of FIG. 2 with the cartridge 20 as detailed by FIGS. 3 and 4, it will be seen that plate 14a electrically corresponds to the split sleeve 31 whereas plate 14b corresponds to the cartridge 20 grounding plate 21.

Figure 5:
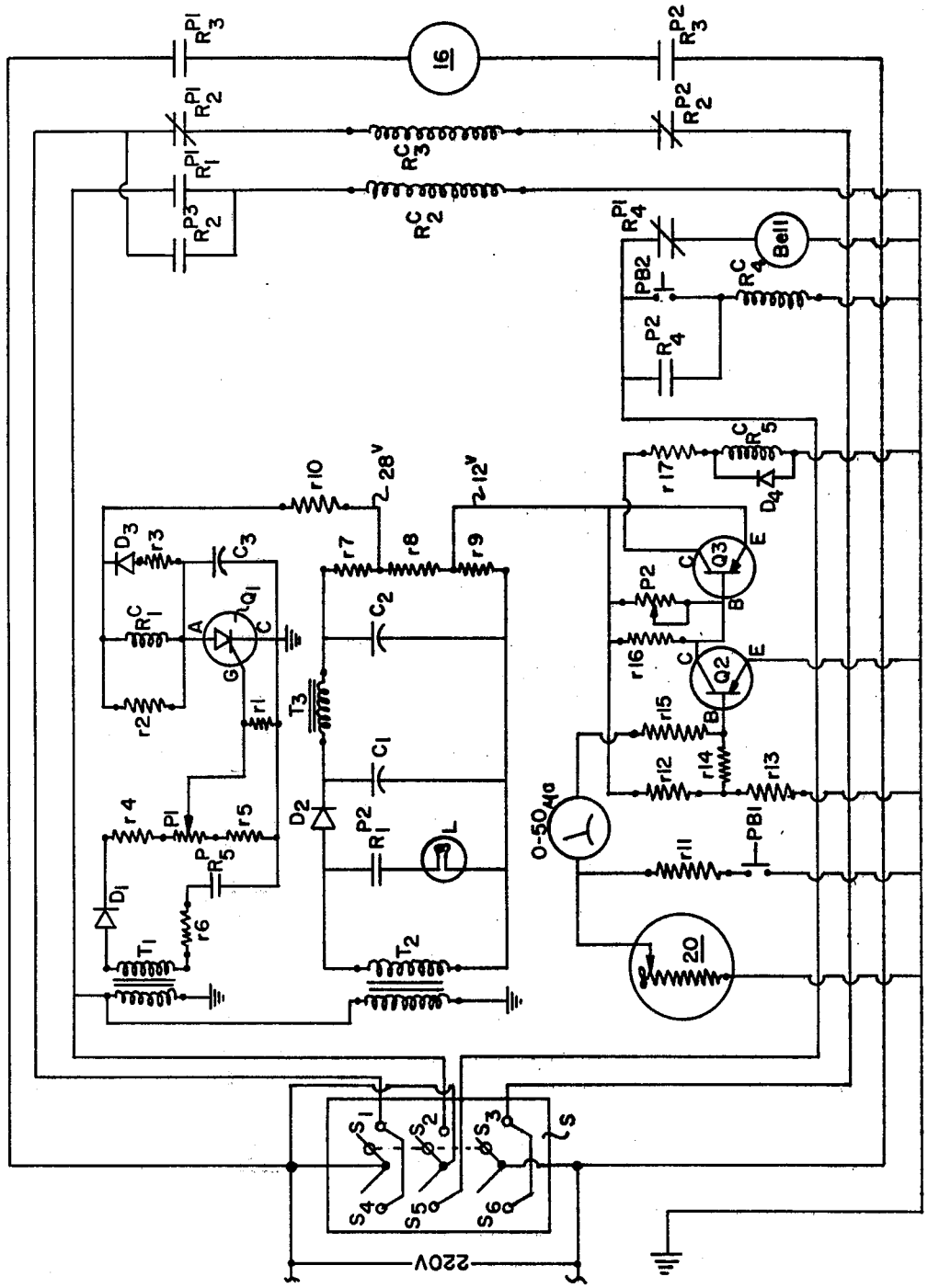
FIG. 5 is a schematic of the electric circuitry preferably used in combination with the sensor of FIGS. 1, 3 and 4.

For control over the filter motor 16 using the cartridge sensor 20 in the FIG. 1 transfer system, a circuit such as that represented by FIG. 5 is used in the control console 200. Master switch S in the circuit s a 3-pole, double-throw, normally open device of the appropriate power rating. The double-throw capacity of switch S permits a manual over-ride of the sensor controlled shutdown operation of the invention. In the normal course of events however, the invention will be operated with switch S in the protected run position which closes the moving contacts with fixed contracts $S_1$ and $S_3$. This event energizes the coil $R_3{}^c$ of a double pole, normally open relay having contact points $R_B{}^{P1}$ and $R_3{}^{P2}$ in line series with the filter motor 16 power circuit. Consequently, motor 16 is started. Pump 15, driven by motor 16, begins the transfer of oil from the carrier 11 through the filter cartridge 12 and into the transformer 10.

So long as the blotter 30 of cartridge 20 remains free of moisture, the remainder of the sensor circuit is open and inoperative. Schematically, sensor 20 is represented in FIG. 5 as a variable-to-infinite potentiometer. Accordingly, the dry state of blotter 30 provides an infinite resistance or open condition in the circuit.

Closure of the protected run contacts of switch S also includes $S_2$ which emergizes transformers $T_1$ and $T_2$ for appropriate voltage reduction. A 12 volt tap is drawn from the $T_1$ power circuit between resistors r8 and r9 to charge the emitter E and base B of transistor $Q_3$. Also charged by the $12^v$ power tap are the collector C and base B of transistor $Q_2$ although the actual voltage at $Q_2$ base B is a reduced value function of the bridge comprising resistors r12 and r14 in one leg and r15 and sensor 20 in the other leg.

The 28 volt tap from the transformer $T_2$ power circuit is connected through the coil of relay $R_1{}^c$ to the A terminal of silicon controlled rectifier (SCR) $Q_1$.

The power circuit of transformer $T_1$ is connected to the gate G of SCR $Q_1$ but is normally held open by points $R_5{}^P$ of a relay.

With the invention operative and the switch S contacts $S_1$, $S_2$ and $S_3$ closed, a small quantity of water in the oil transfer conduit driven by the flow stream against blotter material 30 will be absorbed thereby to reduce the resistance of sensor 20. This event will unbalance the resistance bridge of r12, r14 and r15 thereby permitting a current flow. Such current flow raises the potential at transistor $Q_2$ base B above the conductance threshold which initiates a current flow between collector C and emitter E terminals of $Q_2$. Such current from $Q_2$ raises the voltage on the transistor $Q_3$ base B to start conduction of the $12^v$ potential at emitter E through collector C. $Q_3$ collector C is connected across the coil $R_5{}^c$ of the relay points $R_5{}^P$ in the $T_1$ power circuit. By the energization of coil $R_5{}^c$, points $R_5{}^P$ are closed to charge the gate terminal G of SCR $Q_1$. Characteristically, $Q_1$ starts conduction across terminals A and C thereby creating a current flow through the relay coil $R_1{}^c$.

The $R_1$ relay has two, normally open point sets $R_1{}^{P1}$ and $R_1{}^{P2}$. The point set $R_1{}^{P2}$ is connected to conduct $T_2$ power across an indicator light L. Point set $R_1{}^{P1}$ closes the energy circuit to relay coil $R_2{}^c$.

Relay $R_2$ has three point contact sets, $R_2{}^{P1}$, $R_2{}^{P2}$ and $R_2{}^{P3}$. Sets $R_2{}^{P1}$ and $R_2{}^{P2}$ are connected normally closed in series with relay $R_3$ coil $R_3{}^c$. When $R_2{}^c$ is energized, points $R_2{}^{P1}$ and $R_2{}^{P2}$ open to de-energize coil $R_3{}^c$ thereby opening points $R_3{}^{P1}$ and $R_3{}^{P2}$ which stops filter motor 16.

The third point set $R_2{}^{P3}$ is a normally open set which closes when the coil $R_2{}^c$ is energized. This point set $R_2{}^{P3}$ is connected in the seal-in mode which, when initially closed, assures continued conduction through its own coil $R_2{}^c$.

Termination of the aforedescribed sequence is to leave the filter motor 16 power conduction switches $R_3{}^{P1}$ and $R_3{}^{P2}$ in the open, non-conductive condition with alarm light L illuminated to signal an operator that the transfer unit has been stopped due to the detection of water in the oil.

If, for conscious reasons, the operator desires to operate the filter pump 15 without the protection afforded by the invention, switch S may be closed with the $S_4$, $S_5$ and $S_6$ contacts. This condition energizes coil $R_3{}^c$ to close power contacts $R_3{}^{P1}$ and $R_3{}^{P2}$ but simultaneously energizes an alarm bell in series circuit with the normally closed contact $R_4{}^{P1}$. The audible presence of the bell has the objective of causing the operator to reconsider what he is doing. If, upon reconsideration, the operator desires to continue this mode of operation he may terminate the bell by manually closing the acknowledgment switch PB2 to the $R_4{}^c$ coil which opens points $R_4{}^{P1}$ and closes points $R_4{}^{P2}$ to seal-in the acknowledgment state.

Figure 6:
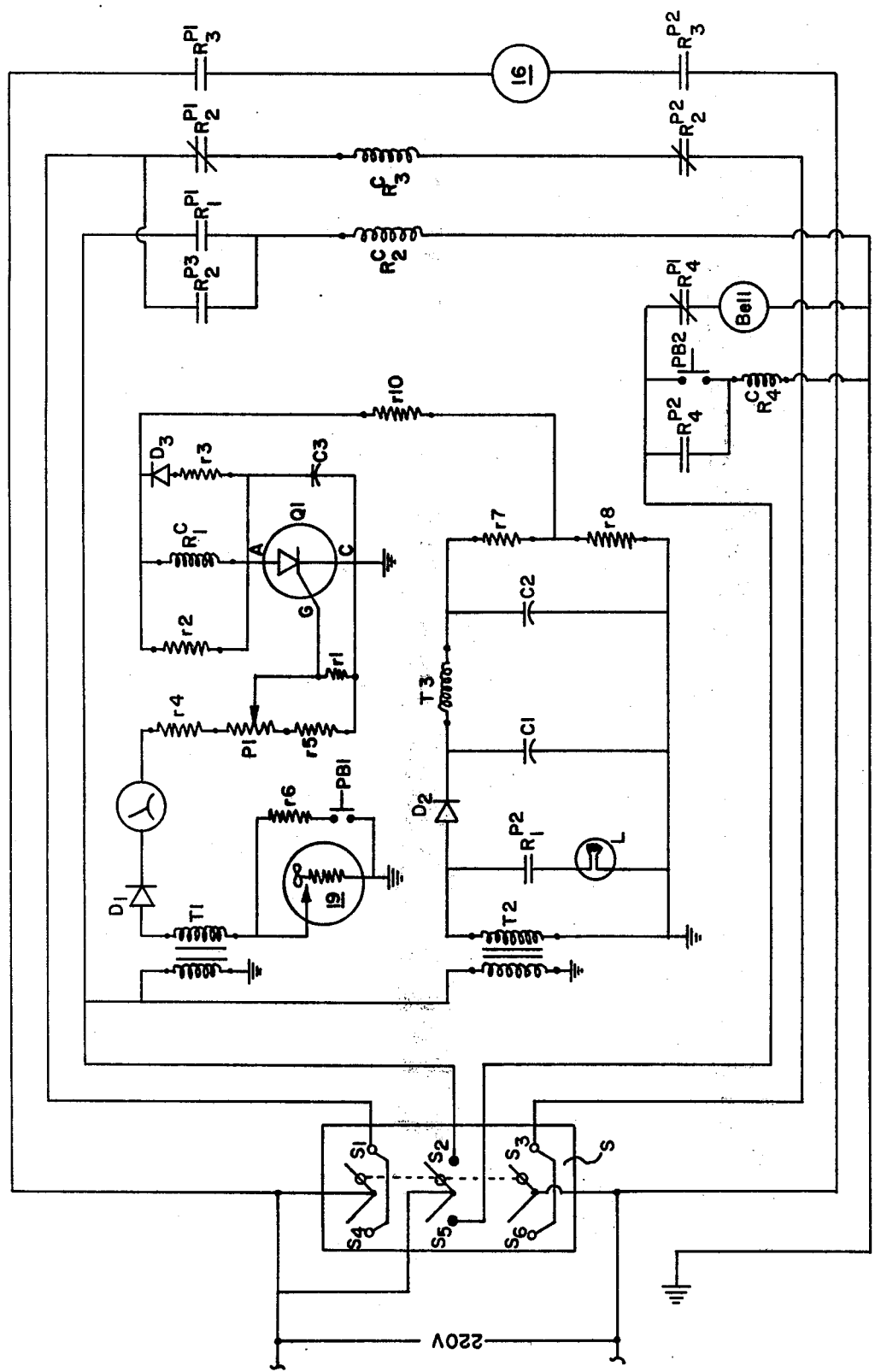
FIG. 6 is a schematic of the electric circuitry preferably used in combination with the filtering sensor of FIG. 2.
Figure 7:
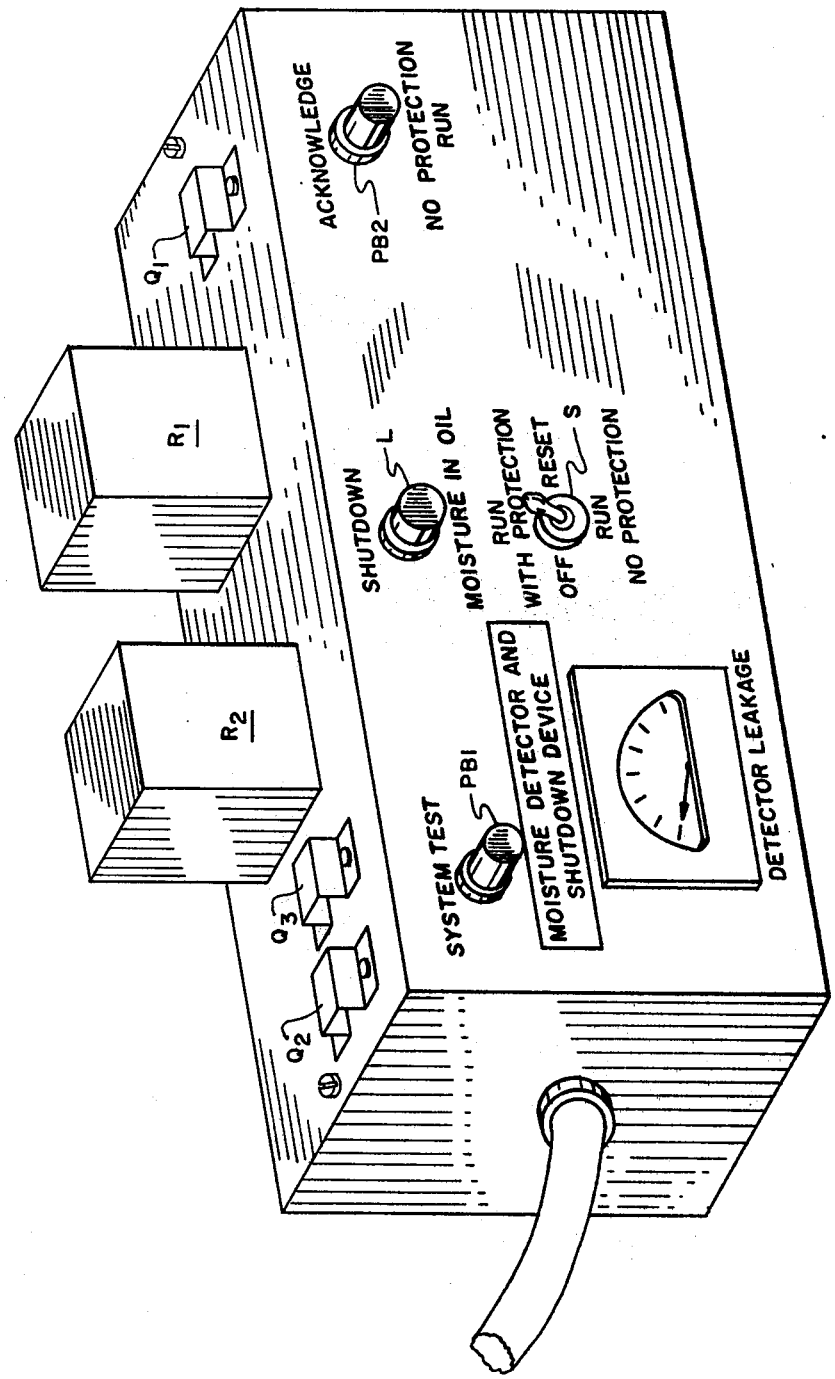
FIG. 7 is a pictorial of a representative control console for the present circuitry.

A simplified, alternative circuit is illustrated by FIG. 6 for the filtering sensor 19 of FIG. 2. In this embodiment of the invention, plate 14a of the filtering sensor 19 is charged directly to transformer $T_1$. Should conduction occur due to water contact with any of the blotter sheets 18, the bias voltage of SCR $Q_1$ gate terminal G is raised to the A-C terminal conductance level. Such conductance energizes relay $R_1$ coil $R_1{}^c$ to close points $R_1{}^{P1}$ and $R_1{}^{P2}$. Points $R_1{}^{P2}$ illuminate the alarm lamp L whereas points $R_1{}^{P1}$ energize the coil $R_2{}^c$ of motor 16 power disconnect circuits as described relative to the FIG. 5 embodiment.

The unprotected operating capacity and acknowledgment subcircuit are the same in the FIG. 6 embodiment as in FIG. 5.

The following tabulation of specifications for circuity components may be related to both circuit embodiments although some of the components are not required of the FIG. 6 embodiment.

CIRCUIT COMPONENT TABLE

| | |
|---|---|
| $Q_1$ | Silicon Controlled Rectifier; GE Type C103YY |
| $Q_2$ | Transistor; GE 52 |
| $Q_3$ | Transistor; RCA SK303 |
| $T_1$ | Transformer; Stancor NOP8616 |
| $T_2$ | Transformer; Stancor NOP8616 |
| $T_3$ | Choke; Stancor NOG2726 |
| $C_1$ | Capacitor; 50v, 50 mfd, Axial lead |
| $C_2$ | Capacitor; 50v, 50 mfd, Axial lead |
| $C_3$ | Capacitor; 50v, 0.01 mfd, disc ceramic |
| $P_1$ | Potentiometer; 5 k$\Omega$, 0.5w |
| $P_2$ | Potentiometer; 5 k$\Omega$, 0.5w |
| r1 | resistor; 1w; 1 k$\Omega$ |
| r2 | resistor; 1w; 2.7 k$\Omega$ |
| r3 | resistor; 1w; 100$\Omega$ |
| r4 | resistor; 1w; 39 k$\Omega$ |
| r5 | resistor; 1w; 1.5 k$\Omega$ |
| r6 | resistor; 1w; 4.7 k$\Omega$ |
| r7 | resistor; 3w; 15$\Omega$ |
| r8 | resistor; 3w; 750$\Omega$ |
| r9 | resistor; 3w; 500$\Omega$ |
| r10 | resistor; 3w; 15$\Omega$ |
| r11 | resistor; 1w; 680 k$\Omega$ |
| r12 | resistor; 1w; 200 k$\Omega$ |
| r13 | resistor; 1w; 200 k$\Omega$ |
| r14 | resistor; 1w; 15 M$\Omega$ |
| r15 | resistor; 1w; 1 k$\Omega$ |
| r16 | resistor; 1w; 1 M$\Omega$ |
| r17 | resistor; 1w; 220$\Omega$ |
| D1 | Silicon Diode; 2.5a |
| D2 | Silicon Diode; 2.5a |
| D4 | Diode IN457 |
| D5 | Dide IN34A |

From the foregoing, it may therefore be seen that the oil flow stream need never be subjected to more than 12 volts d.c. across the respective sensor plate. Once conduction starts through the hydrophilic blotter material 18 or 30, potential across the plates drops to approximately 1 volt d.c. at 3 to 10 $\mu$a. The inherent spark safety of such a low powered sensory system is self-evident.

In tests, the invention has shown a responsive sensitivity to as little as four tablespoons of water dispersed in a 55 gallon quantity of dielectric oil.

Having fully described my invention, alternative embodiments and uses thereof will become readily apparent to those of ordinary skill. The first actuating signal initiated in response to current flow across one embodiment of the water sensor may be used in any appropriate actuating or alarm circuit. Accordingly this signal may also be used to stop an internal combustion engine drive of the pump 15 by interrupting the ignition or fuel supply.

As my invention, therefore,

I claim:

1. A method of charging electric power transmission equipment with dielectric oil comprising the steps of providing a flow conduit between a reservoir of said oil and said equipment, providing a full-flow, hydrophilic filter within said conduit and motor driven pump means to induce flow of said oil through said filter, the improvement comprising the steps of:
   A. Disposing within said conduit, downstream of said filter, water sensing means comprising a pair of electrodes separated by hydrophilic insulating means, said electrodes intimately contacting said insulating means;
   B. Charging an electric potential across said electrodes of insufficient strength to conduct past said insulating means in the absence of water permeation thereof;
   C. Sensing the presence of current flow past said insulating means in the event of water permeation thereof;
   D. Initiating an actuating signal in response to said current flow;
   E. Inactivating said pump motor means in response to said actuating signal.

2. A method as described by claim 1 comprising the improvement steps of:
   A. Providing a first perforated metallic cylinder as one of said electrodes;
   B. Providing a second perforated metallic cylinder concentric of said first as the other of said electrodes;
   C. Wrapping a sheet of said insulating material about said first cylinder and disposing said second cylinder about said wrap to form a sensor assembly; and
   D. Inserting said sensor assembly within said conduit.

3. An apparatus for detecting a dispersed, minute quantity of water in a petroleum fluid comprising:
   A. A pair of first and second concentric perforated metallic cylinder electrode means, said first electrode means being secured at one axial end thereof to fluid container attachment means, said second electrode means being circumferentially expansible for removable, concentric clamping positionment adjacent said first electrode means;
   B. A sheet of water permeable, hydrophilic insulating means cylindrically disposed concentrically between said first and second electrode means, said insulating means being characterized by a reduction of dielectric property when permeated by water;
   C. Electric potential charging means connected across said electrodes;
   D. Potential limiting means to maintain said potential across said electrodes below a conductive level in the absence of water permeation of said insulating means; and,
   E. Current sensing means connected to said electrodes to initiate an actuating signal responsive to current flow across said electrodes.

4. An apparatus as described by claim 3 wherein said sensing means comprises a bridge circuit having at least two resistance legs, one of said legs comprising said charging means across said electrodes, junction means between said legs for providing voltage bias on a base terminal of semiconducting means, said semiconducting having emitter and collector terminals connected to initiate conduction of said actuating signal when said voltage bias on said base rises to a threshold level due to current conduction through the charging means leg of said bridge circuit.

5. Apparatus as described by claim 3 wherein said electrode charging means comprises transformer means having said current sensing means in circuit therewith, said current sensing means comprising a bridge circuit having at least two resistance legs with a conductor junction therebetween, and silicon controlled rectifier means having a gating terminal thereof connected to said junction means and conductive terminals thereof connected to initiate said actuating signal upon current conduction past said insulating means.

6. An apparatus for charging a sealed container of electrical power transmission equipment with dielectric oil, said apparatus comprising:
   A. A supply reservoir for said dielectric oil;
   B. Pump means in a first conduit operatively connected to said reservoir for drawing said oil therefrom and discharging same into a second conduit connected to said sealed container;
   C. Full flow hydrophilic filter means disposed in said second conduit for extracting all water from said oil flowing therethrough; and
   D. Water sensor means in said second conduit between said filter means and said sealed container comprising a pair of perforated metallic electrodes separated in a laminated assembly by a sheet of hydrophilic, water permeable material having a high dielectric strength when dry and low dielectric strength when wet.
   E. Electric potential charging means connected across said sensor electrodes;
   F. Potential limiting means combined with said charging means to maintain said potential across said electrodes below a conductive level in the absence of water permeation of said hydrophilic material; and,
   G. Current sensing means connected to said sensor electrodes that is responsive to current flow across said electrodes due to water permeation of said hydrophilic material for initiating a signal to terminate the operation of said pump means.

7. An apparatus as described by claim 6 wherein said hydrophilic material comprises an approximately 0.025 inch thickness of approximately 26 pounds per cubic foot density cellulose.

* * * * *